United States Patent
McCall, II et al.

(10) Patent No.: US 10,763,588 B2
(45) Date of Patent: Sep. 1, 2020

(54) PATIENT TRACKING SYSTEM FOR MONITORING PATIENT DATA

(71) Applicant: TenX Healthcare, Inc., Sunrise, FL (US)

(72) Inventors: Philip McCall, II, Miramar, FL (US); Kenneth Condren, Parkland, FL (US)

(73) Assignee: TENX HEALTHCARE, INC., Sunrise ( * ) Notice: Subject to any disclaimer, the term of this patent is extended or adjusted under 35 U.S.C. 154(b) by 439 days.

(21) Appl. No.: 15/885,722

(22) Filed: Jan. 31, 2018

(65) Prior Publication Data

US 2018/0219298 A1    Aug. 2, 2018

Related U.S. Application Data

(60) Provisional application No. 62/452,672, filed on Jan. 31, 2017.

(51) Int. Cl.

| | | |
|---|---|---|
| *H01Q 1/52* | (2006.01) | |
| *H01Q 1/24* | (2006.01) | |
| *H01Q 1/27* | (2006.01) | |
| *H01Q 17/00* | (2006.01) | |
| *G06K 19/077* | (2006.01) | |
| *G16H 40/67* | (2018.01) | |
| *G16H 10/65* | (2018.01) | |
| *G16H 10/60* | (2018.01) | |

(52) U.S. Cl.
CPC ....... *H01Q 17/00* (2013.01); *G06K 19/07762* (2013.01); *G06K 19/07771* (2013.01); *G16H 10/65* (2018.01); *G16H 40/67* (2018.01); *H01Q 1/245* (2013.01); *H01Q 1/273* (2013.01); *H01Q 1/526* (2013.01); *G16H 10/60* (2018.01)

(58) Field of Classification Search
CPC ......... H01Q 1/526; H01Q 1/273; H01Q 1/245
See application file for complete search history.

(56) References Cited

U.S. PATENT DOCUMENTS

| | | | | |
|---|---|---|---|---|
| 6,265,977 | B1 * | 7/2001 | Vega | G06K 19/07788 |
| | | | | 340/572.7 |
| 7,102,520 | B2 * | 9/2006 | Liu | G06K 19/07749 |
| | | | | 340/572.1 |
| 7,646,304 | B2 * | 1/2010 | Cote | G06K 19/07718 |
| | | | | 257/700 |

(Continued)

*Primary Examiner* — Hung V Ngo
(74) *Attorney, Agent, or Firm* — The Plus IP Firm; Derek Fahey, Esq.

(57) ABSTRACT

A shield, when coupled to a tracker device that is worn by an individual, reduces interfering signals originating from the human body that can adversely impact the detection of signals transmitted by the tracker device. The shield can include multiple layers of components. Specifically, the shield includes a base component that is attached to an adhesive element on the first side of the base and covered by a removable backing. Furthermore, the base, through a second side of the base, is attached to a first non-conductive element, which is further coupled to a second non-conductive element. Each of the non-conductive elements attenuates interfering signals that originate from the human body and therefore, enables the detection of signals transmitted by the patient tracking system. For example, in view of the reduced interference signals, a RF signal transmitted by the patient tracking system can be detected at remote distances.

22 Claims, 10 Drawing Sheets

(56) References Cited

U.S. PATENT DOCUMENTS

| | | | | |
|---|---|---|---|---|
| 8,616,459 B2* | 12/2013 | Sykko | .............. | G06K 19/07758 |
| | | | | 235/492 |
| 9,070,066 B1* | 6/2015 | Oliver | .............. | G06K 19/07756 |
| 9,076,092 B2* | 7/2015 | Ritamäki | ......... | G06K 19/07786 |
| 9,947,988 B2* | 4/2018 | Takashima | ........... | H01Q 1/2291 |
| 10,314,506 B2* | 6/2019 | Korkala | ............... | A61B 5/0245 |
| 2004/0217865 A1* | 11/2004 | Turner | ............... | G06K 19/0702 |
| | | | | 340/572.7 |
| 2014/0124582 A1* | 5/2014 | Kroener | ............ | G06K 19/0723 |
| | | | | 235/487 |

* cited by examiner

PATIENT TRACKING SYSTEM FOR MONITORING PATIENT DATA

CROSS-REFERENCE TO RELATED APPLICATION

This application claims the benefit of U.S. Provisional Application No. 62/452,672, filed Jan. 31, 2017. The content of the above referenced application is incorporated by reference in its entirety.

BACKGROUND

The disclosure generally relates to the field of medical devices, and more specifically to a shield of a patient tracking system that reduces conductive signal interference originating from a human body.

Radio Frequency Identification (RFID) systems can be used in many ways for locating and identifying objects. RFID systems are particularly useful in product-related and service-related industries for tracking large numbers of objects are being processed, inventoried, or handled. In such applications, an RFID tag is usually attached to individual items, or to their packages or containers. A conventional RFID system typically includes at least one RFID transmitter (e.g., RFID tag), at least one RFID Reader (or interchangeably referred to as interrogator), and at least one controller or server. The readers inventory the tags and forward the data to the server or controller.

One major limitation of RFID transmitters is the effect of the human body on an RFID transmitter. Since the human body is electrically conductive, the human body can interfere with the signal emitted by a RFID transmitter. Thus, when an RFID transmitter is close to the human body, RFID reader must be brought into proximity (e.g., several feet) of a RF transmitter in order to communicate with the RFID transmitter. A variety of different insulators have been used with RFID transmitters to decrease the effect of conductive materials on the transmitters. However, many of those apparatus and systems are bulky and expensive. As a result, there is a need for an improved method and apparatus to more effectively and efficiently use RFID transmitters in the medical field, and particularly for use when monitoring patients.

SUMMARY

A patient tracking system includes a tracker device and a shield that can be coupled to one another to minimize conductive, interfering signals that originate from the human body. By reducing conductive signals, the shield reduces the adverse impact that the conductive signals have on signals emitted by RFID transmitters located on patient tracking systems that are employed for collecting, monitoring, storing, and tracking patient data. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The patient tracking system includes a tracker device and a shield that attenuates interfering signals from the human body that adversely affects the performance of a RFID transmitter which, in various embodiments, can be located on either the tracker device or on the shield. The shield is composed of multiple layers including one or more non-conductive elements that attenuate the interference signal originating from a human body. Therefore, when the non-conductive elements are positioned between the RFID transmitter and the human body, the non-conductive elements enables the RFID transmitter to effectively communicate with a corresponding RFID reader at distances (e.g., 20 feet and beyond) that are significantly further than conventional systems.

Generally, an attaching feature is used for coupling the shield to the tracker device. In one embodiment, the attaching feature may be an adhesive layer of the shield that is covered by a removable backing. When the removable backing is removed, the adhesive layer can contact and couple with a portion of the tracker device. In another embodiment, the attaching feature may be two openings on the shield. The openings allow a portion of the tracker device to pass through such that the base spans at least a portion of the tracker device. In another embodiment, clips having clamping features may be used as a locking feature or an attaching feature to facilitate maintaining the shield on the tracker device, especially in a single or desired location.

The patient tracking system is for use with a medical document container. The medical document container can be configured to display medical records of a patient as well as patient information collected by the patient tracking system. The medical document container can be communicatively coupled with the patient tracking system such that patient information can be transferred from the patient tracking system to the medical document container. For example, the medical document container may include an RFID reader that transmits a RF signal to the patient tracking system. In response, the patient tracking system transmits a response that includes patient information back to the RFID reader of the medical document container. Thus, the medical document container can continuously track the patient and relevant patient information via transmitted RF signals between the medical document container and the patient tracking system. Additionally, the medical document container can be communicatively coupled to a database that stores electronic patient records. As an example, a database can hold all electronic patient records of a hospital. The medical document container can communicate the patient information for storage in the electronic patient records of the database.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

The figures depict various embodiments of the present invention for purposes of illustration only. One skilled in the art will readily recognize from the following discussion that alternative embodiments of the structures and methods illustrated herein may be employed without departing from the principles of the invention described herein.

The figures use like reference numerals to identify like elements. A letter after a reference numeral, such as "500A," indicates that the text refers specifically to the element having that particular reference numeral. A reference numeral in the text without a following letter, such as "500," refers to any or all of the elements in the figures bearing that reference numeral (e.g. "computing device 500" in the text refers to reference numerals "computing device 500A" and/or "computing device 500B" in the figures).

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems described above by providing a shield that decreases signal interference originating from a human body. The shield prevents the interference from the human body from adversely affecting the signal emitted by a RFID transmitter. The signal emitted by the RFID transmitter can include various patient data including the patient's location, patient's vital signs, patient's activity, patient's behavior, and the like. A tracker device can be embodied as a wristband, a necklace, a headband, an implant, an article of clothing, and the like. In one embodiment, the tracker device can be medical equipment in a hospital such as one of a bedpost, a tray, a mobile device, imaging equipment, and the like. In these embodiments, the tracker device, when coupled with a shield, enables the tracking of equipment used by patients, which may be a reflection of the patient's recent activities. Altogether, the shield enables hospitals and other medical facilities to more accurately track patients and/or equipment associated with the patients.

Figure 1:
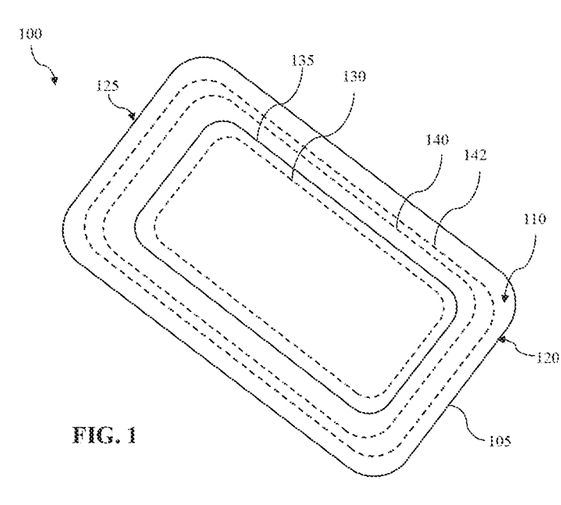
FIG. 1 is a top view of a shield for use with a patient tracking system for collecting, monitoring, storing, and tracking patient data, according to one example embodiment.

Referring now to the Figures, FIG. 1 is a top view of the shield 100 for use with a patient tracking system for collecting, monitoring, storing and tracking patient data. Further reference is made to FIG. 1A which is a side view of the shield 100, in accordance with an embodiment. The shield 100 can include multiple components that form individual layers of the shield 100. In the embodiment shown in FIG. 1, the shield 100 includes a first non-conductive element 140, a second non-conductive element 142, a base 105, an adhesive element 130, and a removable backing 135. In various embodiments, there may be additional or fewer components in the shield 100. As an example, the shield 100 may include a single non-conductive element.

In various embodiment, the components of the shield 100 are composed of material that enable each component to bend such that the curvature of the bent shield 100 enables the shield 100 to remain in contact with any curved portions of the human body. For example, the shield 100 may bend to remain in contact with the wrist of the human body.

In the embodiment shown in FIG. 1, each of the components can be quadrilateral in shape; however in other embodiments, each of the components may be differently shaped. Each of the components may also possess rounded corners to reduce any adverse effects that may be experienced by the patient (e.g., scratches, injuries, irritants) due to the shape of the components of the shield 100.

Figure 1A:
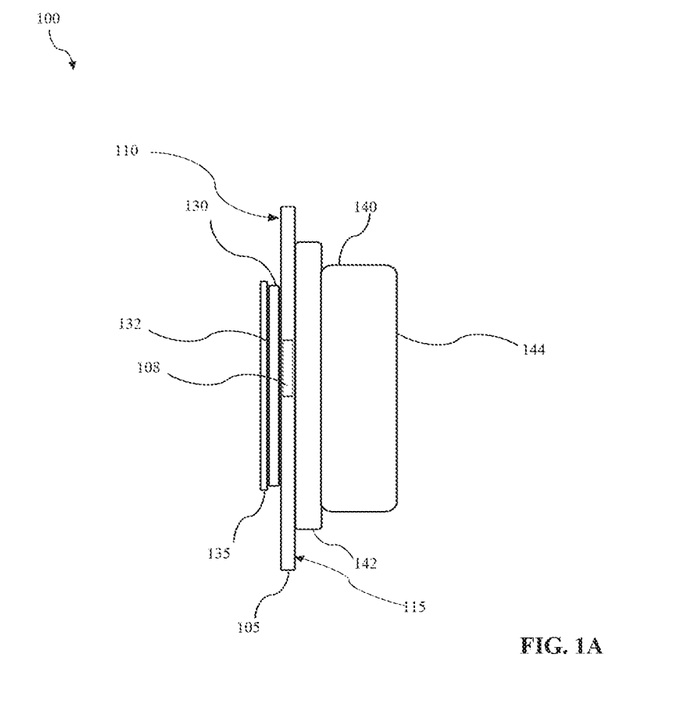
FIG. 1A is a side view of the shield, according to one example embodiment.

Each of the components of the shield 100 can be sequentially arranged as layers. As shown in FIG. 1A, from right to left, the layers of the shield 100 can include the first non-conductive element 140, the second non-conductive element 142, the base 105, the adhesive element 130, and the removable backing 135. Unless explicitly described below, each of the components can be coupled with an adjacent component in the shield 100 through one of an adhesive (e.g., glue, tape, VELCRO) or a fastener.

In various embodiments, as shown in FIG. 1A, the first non-conductive element 140 of the shield 100 includes an exposed surface 144 and is further coupled to the second non-conductive element 142. When an individual wears a patient tracking system that includes the shield 100 that is coupled with the tracker device, the exposed surface 144 of the non-conductive element 140 is located proximal to the human body of the individual in comparison to other components of the shield 100 and the tracker device. The non-conductive element 140 serves to reduce interference emitted from the human body. More specifically, the non-conductive element 140 can serve to shield a RFID transmitter, such as an RFID element of the base 105, from interference that originates from the human body. The non-conductive element 140 may comprise any non-conductive materials or combinations of materials such as polystyrene, polyisocyanurate, polyurethane, cellulose, fiberglass, ethylene vinyl acetate, polyethylene and the like. However, other non-conductive elements are also within the spirit and scope of the present invention.

The first non-conductive element 140 of the shield 100 may be composed of a material with a first density. In various embodiments, the first density of the first non-conductive element 140 is between 3 kg/m$^3$ and 50 kg/m$^3$. In some embodiments, the first density of the first non-conductive element 140 is between 5 kg/m$^3$ and 40 kg/m$^3$. In some embodiments, the first density of the first non-conductive element 140 is between 8 kg/m$^3$ and 30 kg/m$^3$. In some embodiments, the first density of the first non-conductive element 140 is between 10 kg/m$^3$ and 20 kg/m$^3$.

In some embodiments, the first density of the first non-conductive element 140 is between 14 kg/m³ and 16.5 kg/m³.

The first non-conductive element 140 may have a particular thickness. In various embodiments, the thickness of the first non-conductive element 140 is between 0.25 inches and 0.625 inches. In various embodiments, the thickness of the first non-conductive element 140 is between 0.30 inches and 0.575 inches. In various embodiments, the thickness of the first non-conductive element 140 is between 0.35 inches and 0.525 inches. In various embodiments, the thickness of the first non-conductive element 140 is between 0.40 inches and 0.475 inches.

In various embodiments, the first non-conductive element 140 may have a length between 2 and 4 inches. In some embodiments, the length of the first non-conductive element 140 is between 2.5 and 3.5 inches. In some embodiments, the width of the first non-conductive element 140 is between 0.75 and 1.5 inches. In some embodiments, the width of the first non-conductive element 140 is between 0.10 inches and 0.125 inches.

The second non-conductive element 142 of the shield 100 is coupled to the first non-conductive element 140. As shown in FIG. 1A, the second non-conductive element 142 is the layer of the shield 100 that is adjacent to the layer of the first non-conductive element 140. Similar to the first non-conductive element 140, the second non-conductive element can also serve to reduce interference from the human body and can comprise any materials or combination of materials such as polystyrene, polyisocyanurate, polyurethane, cellulose, fiberglass, ethylene vinyl acetate, polyethylene, and the like.

In various embodiments, the second non-conductive element 142 of the shield 100 may be composed of a material with a second density. In various embodiments, the second density of the second non-conductive element 142 is between 50 kg/m³ and 250 kg/m³. In some embodiments, the second density of the second non-conductive element 142 is between 70 kg/m³ and 200 kg/m³. In some embodiments, the second density of the second non-conductive element 142 is between 80 kg/m³ and 180 kg/m³. In some embodiments, the second density of the second non-conductive element 142 is between 100 kg/m³ and 150 kg/m³. In some embodiments, the second density of the second non-conductive element 142 is between 120 kg/m³ and 130 kg/m³.

Generally, the second density of the second non-conductive element 142 is greater than the first density of the first non-conductive element 140. By designing the first non-conductive element 140 and the second non-conductive element 142 in this manner, the combination of the first non-conductive element 140 and the second non-conductive element 142 attenuates more human body interference in comparison to the attenuation achieved by a single non-conductive element.

The second non-conductive element 142 may have a particular thickness. In various embodiments, the thickness of the second non-conductive element 142 is between 0.05 inches and 0.25 inches. In various embodiments, the thickness of the second non-conductive element 142 is between 0.10 inches and 0.175 inches. In various embodiments, the thickness of the second non-conductive element 142 is between 0.12 inches and 0.15 inches.

Generally, the first non-conductive element 140 may have a thickness that is greater than the thickness of the second non-conductive element 142.

In various embodiments, the second non-conductive element 142 may have a length between 2 and 4 inches. In some embodiments, the length of the second non-conductive element 142 is between 2.5 and 3.5 inches. In some embodiments, the width of the second non-conductive element 142 is between 0.75 and 1.5 inches. In some embodiments, the width of the second non-conductive element 142 is between 0.10 inches and 0.125 inches.

Additionally, in various embodiments, the dimensions of the second non-conductive element 142 may be larger than the dimensions of the first non-conductive element 140. For example, as shown in FIG. 1, the length and width of the second non-conductive element 142 are larger than the length and width of the first non-conductive element 140, respectively.

In various embodiments, the second non-conductive element 142 and the first non-conductive element 140 need not be adjacent layers in the shield 100. In one embodiment, the base 105 is positioned between the first non-conductive element 140 and the second non-conductive element 142.

Referring now to the base 105, as shown in FIG. 1, the base 105 has a first end 120 and an opposing second end 125. Furthermore, as shown in FIG. 1A, the base 105 has a first side 110 and an opposing second side 115. In various embodiments, the base 105 may comprise a material such as a plastic, polypropylene, polyvinyl chloride (PVC) plastic, vinyl, silicone, and the like. As shown in FIG. 1, the base 105 may be the component of the shield 100 that has the largest dimensions in comparison to the dimensions of other components of the shield 100. Specifically, the width of the base 105 and the length of the base 105 may be greater than the width and length, respectively, of each of the other components of the shield 100. Therefore, when a user handles the shield 100, the user can contact and manipulate the base 105 as opposed to contacting other elements of the shield 100.

In various embodiments, the base 105 has a particular density that is greater than the first density of the first non-conductive element 140 and less than the second density of the second non-conductive element 142. In one embodiment, the base 105 has a density between 500 and 1,500 kg/m³. In one embodiment, the base 105 has a density between 750 and 1,250 kg/m³. In one embodiment, the base 105 has a density between 900 and 1,000 kg/m³.

The second non-conductive element 142 may have a particular thickness. In various embodiments, the thickness of the base 105 is between 0.01 inches and 0.05 inches. In various embodiments, the thickness of the base 105 is between 0.02 inches and 0.04 inches. In various embodiments, the thickness of the base 105 is approximately 0.03 inches.

In various embodiments, the base 105 may have a length between 3 and 5 inches. In some embodiments, the length of the base 105 is between 3.5 and 4.5 inches. In some embodiments, the width of the base 105 is between 1 and 2 inches. In some embodiments, the width of the base 105 is between 1.25 inches and 1.75 inches.

In various embodiments, the base 105 further includes an RFID element 108. The RFID element 108 is located on the base 105 such that when the shield 100 is coupled to the tracker device and worn by an individual, the RFID element 108 is separated from the individual by the first non-conductive element 140 and the second non-conductive element 142. The RFID element 108 may be a circuitry that is inlaid on the base 105. The RFID element 108 is configured to receive a RF signal and to transmit data in response to the RF signal. For example, the RFID element 108 includes an RFID tag that can be any one of an active tag, passive tag, or a semi-passive tag. In one embodiment, the RFID element 108 includes an active RFID tag and therefore, further includes a battery power in the circuitry. In one embodiment, the RFID element 108 includes a passive tag and therefore, is powered by the signal energy transmitted by a corresponding RFID reader. Further detail of a corresponding RFID reader is described below in relation to the medical document container in FIG. 4.

When the RFID element 108 receives a signal from the RFID reader, the RFID element 108 responds by transmitting a response to the RFID reader. In various embodiments, the RFID tag can be assigned a unique serial number and therefore, the transmitted response can include the unique serial number of the RFID tag. In various embodiments, the transmitted response can include patient information, such as information indicating the location of the RFID element 108 or patient information gathered by the tracker device. The tracker device is described in further detail below in relation to FIG. 2.

In various embodiments, the RFID element 108 is configured to respond to a RF signal of a particular frequency. In one embodiment, the RFID element 108 responds to a low frequency RF signal (e.g., 125 kHz or 134 kHz). In one embodiment, the RFID element 108 responds to a high frequency RF signal (e.g., 13-14 MHz). Here, the RFID element 108 may rely on inductive coupling to generate a transmitted response. In one embodiment, the RFID element 108 responds to an ultra-high frequency RF signal (e.g., 860-960 MHz). Here, the RFID element 108 may rely on far-field coupling to achieve communication with the RFID reader across large distances (e.g., 20 meters and above).

The adhesive element 130 may include a surface 132 that is configured with an adhesive. The adhesive may be a pressure sensitive adhesive comprising materials such as comprise lanolin, mineral oil, petrolatum, rosin, silicone, and zinc oxide. The surface 132 can be in contact with a removable backing 135. In various embodiments, as shown in FIG. 1A, the adhesive element 130 is further coupled to the first side 110 of the base 105.

The removable backing 135 may be comprised of a material, such as wax paper or other materials used to protect adhesive materials. The removable backing 135 is configured to be removed to expose the adhesive element 130 such that the surface 132 of the adhesive element 130 can be adhered to the tracker device 200.

Figure 1B:
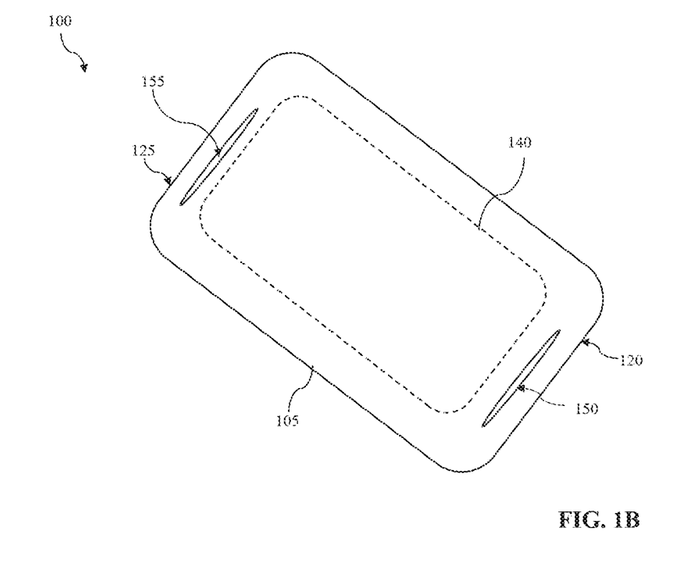
FIG. 1B is a top view of the shield, according to a second example embodiment.

Reference is now made to FIGS. 1B and 1C which depict a top view and a perspective view, respectively, of the shield 100, according to a second embodiment. In these embodiments, the shield 100 includes a base 105 and one or more non-conductive elements 140. The shield 100 need not include an adhesive element 130 or removable backing 135. The base 105 includes one or more openings 150 and 155. In various embodiments the base 105 includes one opening 150 or 155 located on one end (e.g., either first end 120 or second end 125) of the base 105. The single opening can enable a portion of the tracker device to enter through the opening 150 or 155 and to couple with the shield 100. For example, if the tracker device is to be worn as a necklace, a portion of the tracker device necklace can be configured to pass through the opening 150 or 155 of the base 105 to couple with the shield 100.

In the embodiment shown in FIG. 1B, opening 150 is located at the first end 120 of the base 105 and opening 155 is located at the second end 125 of the base 105. Each opening 150 and 155 can be a slit, however in other embodiments, each opening 150 and 155 can be differently shaped. The openings 150 and 155 are configured to enable a portion of the tracker device to couple with the shield 100. For example, if the tracker device is a wristband, the band of the wristband can thread through the openings 150 and 155 such that the base 105 spans at least a portion of the wristband.

Figures 2, 2A:
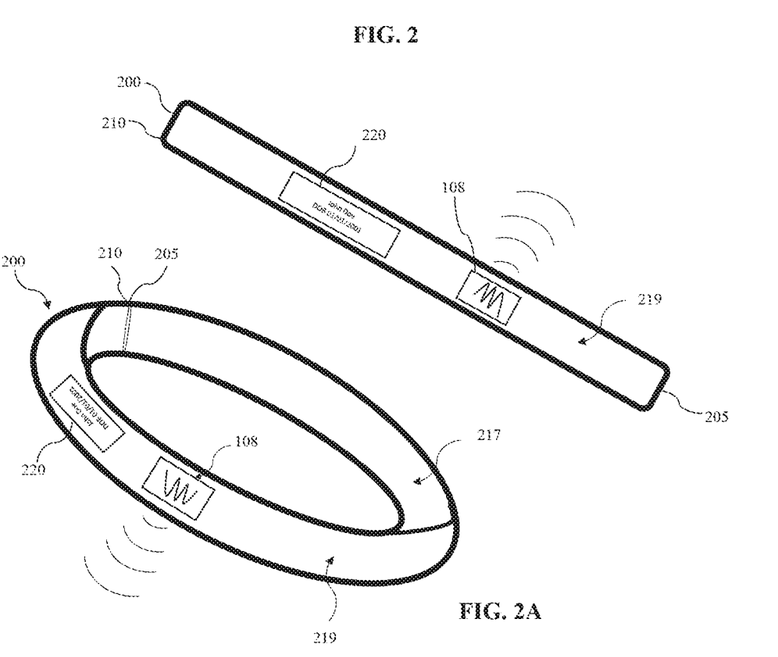
FIG. 2 is a perspective view of a tracker device, according to an example embodiment.
FIG. 2A is a perspective view of the tracker device in a looped configuration, according to an example embodiment.

FIG. 2 is a perspective view of the tracker device 200, in accordance with an embodiment. The tracker device 200 can be a device worn by a patient and can be configured to collect patient information. For example, FIG. 2 depicts a wearable wristband tracker device 200. Here, the tracker device 200 can collect patient information such as patient vitals (e.g., heart rate). In other embodiments, the tracker device 200 can be a different system or device such as a necklace, a headband, an article of clothing, and the like. In the embodiment shown in FIG. 2, the tracker device 200 comprises a body having a first end 205 and an opposing second end 210, identifying information 220, an outer surface 219, and an inner surface 217 (see FIG. 2A). In some embodiments, instead of the RFID element 108 being included on the shield 100, as is described above, the tracker device 200 includes the RFID element 108 having an RFID transmitter configured to emit a signal that is to be received by a RFID receiver. In other embodiments, the tracker device 200 need not include the RFID element 108.

The identifying information 220 is displayed on a portion of the tracker device 200. Patient information can include patient medical history (e.g., treatment history, prescription history, history of indications, drug usage, and the like), patient personal information (e.g., name, address, date of birth, and the like), and administrative information (e.g., physical location of the patient tracking system, name of medical personnel that is responsible for the patient, and the like). In various embodiments, the identifying information 220 can be located on an adhesive that is adhered to the outer surface 219 of the tracker device 200. Therefore, when the tracker device 200 is worn by a user, the identifying information 220 faces outward on the outer surface 219 such that medical personnel and others may readily identify the patient based on the identifying information 220. In various embodiments, the identifying information 220 is part of the patient information that is transmitted by the RFID element 108 when a RF signal is received.

As shown in FIG. 2A, each end 205 and 210 of the tracker device 200 can be coupled together to form a looped configuration. Thus, the tracker device 200 can be worn by the individual (e.g., on the individual's wrist). When worn, the inner surface 217 of the tracker device 200 is located closer to the individual in comparison to the outer surface 219 of the tracker device 200.

Figure 3:
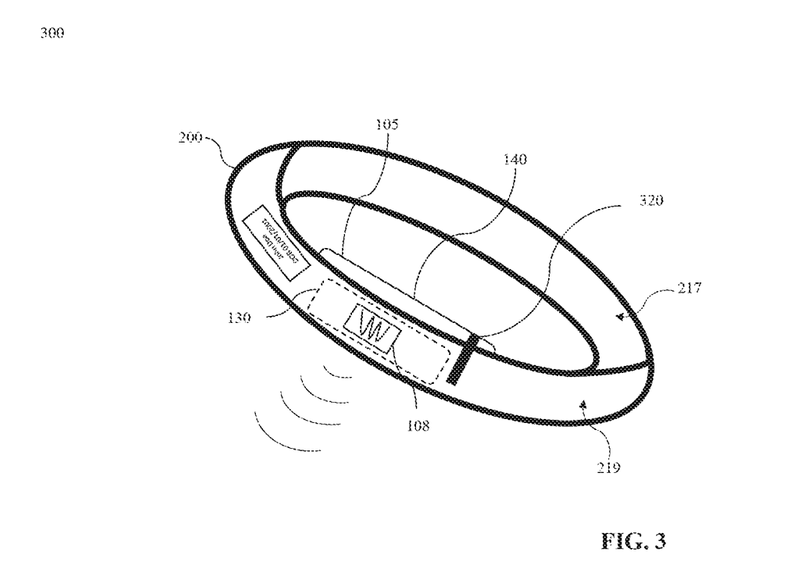
FIG. 3 is a perspective view of the patient tracking system, according to an example embodiment.

FIG. 3 is a perspective view of the patient tracking system 300 which includes the shield 100 coupled to the tracker device 200, according to an example embodiment. In the coupled configuration, the first non-conductive element 140 of the shield 100 is positioned such that if the tracker device 200 is worn by an individual, the first non-conductive element 140 is positioned between the RFID element 108 and the individual's body, thereby decreasing the interference originating from the human body that may adversely affect the RFID element 108.

In accordance with the embodiment of the shield 100 depicted in FIG. 1, the shield 100 can be coupled to the tracker device 200 through the adhesive element 130 of the shield 100. As shown in FIG. 3, the adhesive element 130 (outlined by the dotted lines) can be adhered to the inner surface 217 of the tracker device 200.

To achieve the configuration of the shield 100 and tracker device 200 shown in FIG. 3, the removable backing 135 (see FIG. 1) is removed from the adhesive element 130. Next, the adhesive surface 132 of the adhesive element 130 is contacted with the inner surface 217 of the tracker device 200. Therefore, returning to FIG. 1A, the first side 110 of the base 105 faces the inner surface 217 of the tracker device 200.

In various embodiments, the shield 100 can be additionally or alternatively coupled to the tracker device 200 through a clip 320. Such a clip 320 can have clamping properties to secure the shield 100 to the tracker device 200. In various embodiments, the clip 320 is positioned to securely immobilize the non-conductive element 140 of the shield 100 relative to the RFID element 108 and to the tracker device 200. In some embodiments, more than one clip may be used. In some embodiments, any combination of slots, adhesives, or clips may be used.

Figure 3A:
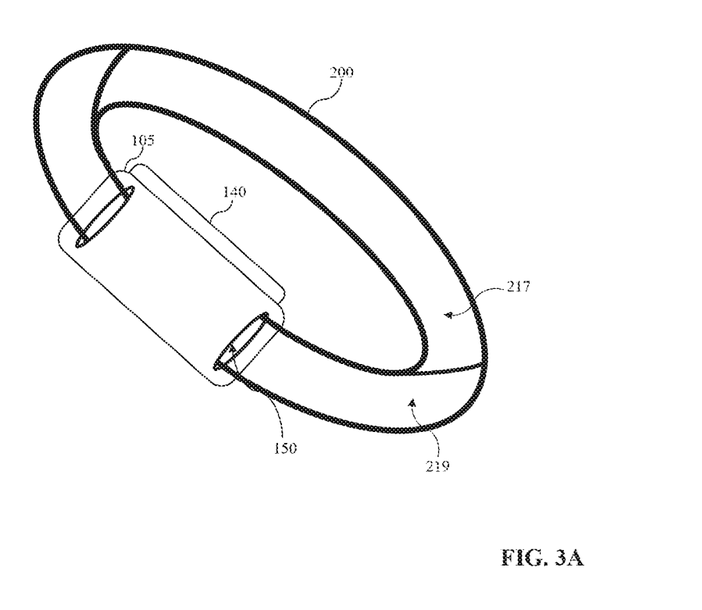
FIG. 3A is a perspective view of the shield attached to a tracker device, according to a second example embodiment.

FIG. 3A is a perspective view of the shield 100 attached to a tracker device 200, according to the second example embodiment shown in FIG. 1B. Here, the base 105 of the shield 100 can include openings 150 and 155 at the ends 120 and 125, respectively, of the base 105. In one embodiment, the openings 150 and 155 are configured to allow the tracker device 200 to pass through such that the base 105 spans along at least a portion of the inner surface 217 of the tracker device 200. In one embodiment, if the tracker device 200 is a wristband, the length of the openings 150 and 155 are sized such that the band of the tracker device 200 can enter through each opening 150 and 155.

Figure 3B:
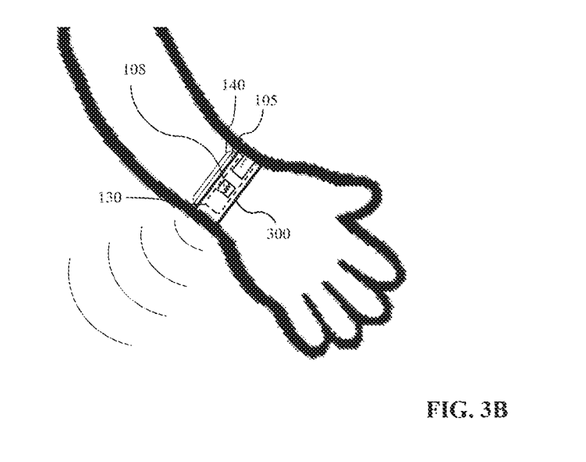
FIG. 3B is a perspective view of the patient tracking system worn by an individual, according to an example embodiment.

FIG. 3B is a perspective view of the patient tracking system 300 worn by an individual, according to an embodiment. More specifically, FIG. 3B illustrates the shield 100 and wristband tracker device 200 that is in accordance with the embodiment shown in FIG. 3. When the shield 100 is coupled to the tracker device 200 and worn by an individual, the non-conductive element 140 is positioned between the RFID element 108 and the human's wrist. In this configuration, the non-conductive element 140, acts as an insulator thereby reducing interference from the human body that would act on the RFID transmitter of the RFID element 108.

Figure 4:
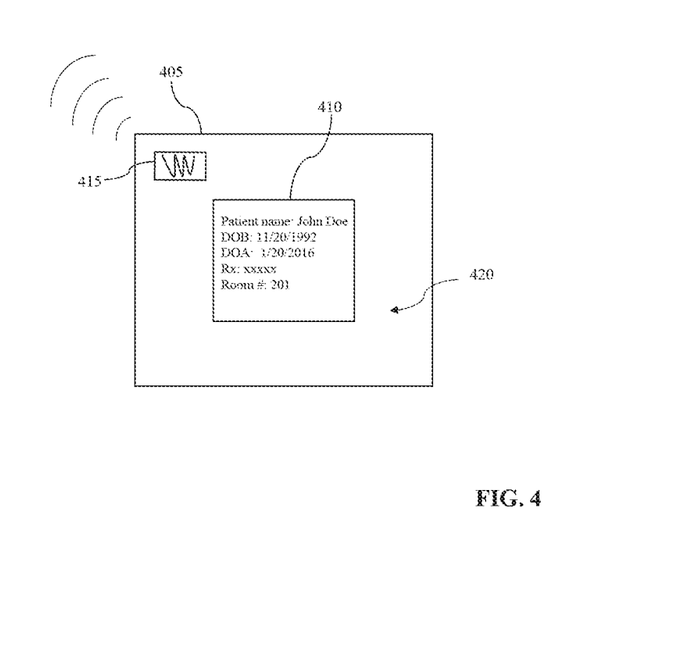
FIG. 4 is a perspective view of a medical document container for use with a patient tracking system, according to example embodiment.

FIG. 4 is a perspective view of a medical document container 405 for use with a patient tracking system 300, according to example embodiment. In one embodiment, the medical document container 405 can be an electronic device, such as a tablet, mobile device, and the like. As shown in FIG. 4, the medical document container 405 may include a first side 420, records 410, and an RFID reader 415.

The medical document container 405 is communicatively coupled to the RFID element 108 of the patient tracking system 300. For example, the RFID reader 415 can be configured to generate and transmit a RF signal with a particular frequency, such as one of a low frequency, high frequency, or ultra-high frequency. In addition, the RFID reader 415 is further configured to detect a response from the patient tracking system 300 that includes patient information collected by the patient tracking system 300. In one embodiment, the RFID reader 415 is located internally within the medical document container 405. In other embodiments, the RFID reader 415 is coupled to an external location of the medical document container 405.

In some embodiments, the medical document container 405 can be remotely located relative to the tracker device 200. For example, the medical document container 405 can be stored at a location (e.g., at a receptionist desk, or a particular location in the hospital) such that a caretaker (e.g., doctor or nurse) can access the medical document containers 405 of various patients. In other embodiments, the medical document container 405 can be located in proximity to the tracker device 200. For example, the medical document container 405 can be located in the same hospital room (e.g., on a table, on a shelf, in a bin on the door).

In various embodiments, the medical document container 405 can be communicatively coupled with a computing device. In one embodiment, the computing device is a database that stores patient information. In another embodiment, the computing device can be a client device operated by a health care provider. The medical document container 405 can transmit information, such as patient information, to be utilized by the computing device or client device. An example computing device is described in further detail below in relation to FIG. 5B. In one embodiment, the medical document container 405 can communicate with the computing device via a communications network (e.g., BLUETOOTH, WiFi, 2G, 3G, 4G, LTE). In one embodiment, the medical document container 405 can communicate with the computing device via RF signals. For example, the medical document container 405 may include a second RFID tag (e.g., a RFID tag that differs from the RFID tag of RFID element 108 described above). Therefore, the second RFID tag of the medical document container 405 can respond to a RF signal transmitted by a RFID reader of the computing device. The second RFID tag of the medical document container 405 can provide patient information received from the patient tracking system 300 in the response to the RF signal.

As shown in FIG. 4, the first side 420 of the medical document container 405 can include the records 410 of a patient. In various embodiments, the first side 420 may be a display screen that is configured to display the records 410 of a patient. In various embodiments, the records 410 include patient information, such as patient information received from the patient tracking system 300 via the RFID reader 415. Therefore, the medical document container 405 can maintain the most up-to-date records 410 of the patient. For example, if the patient's location changes, the up-to-date information of the patient's information can be maintained by the medical document container 405 and displayed as records 410.

Figure 5A:
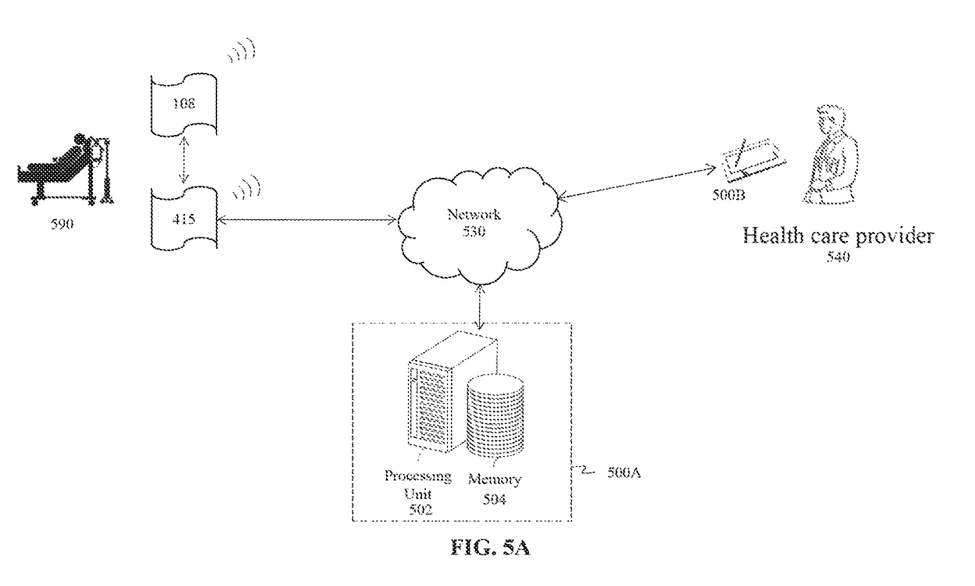
FIG. 5A is a diagram of an overall system environment in which the patient tracking system operates, in accordance with an embodiment.

FIG. 5A is a diagram of an overall system environment in which the patient tracking system operates, in accordance with an embodiment. Here, the RFID element 108 of the patient tracking system 300 can be communicatively coupled with the RFID reader 415 of the medical document container 405. As discussed above, the RFID reader 415 can transmit a RF signal to the RFID element 108 which responds with patient information, such as the location of the patient 590.

The RFID reader 415 is further communicatively coupled with one or both of a computing device 500A or a computing device 500B that is operated by a health care provider 540 through the network 530. The computing device 500A can include a processing unit 502 and a memory 504 and in various embodiments, functions as a database that stores electronic patient records of patients (e.g., patient 590). In one embodiment, the RFID reader 415 can provide patient information of the patient 590 received from the RFID element 108 to the computing device 500A. Therefore, the patient information can be stored with an electronic patient record of the patient 590. In one embodiment, the RFID reader 415 can provide patient information of the patient 590 received from the RFID element 108 to the computing device 500B. Thus, the health care provider 540 that accesses the computing device 500B can have access to the up-to-date patient information.

The network 530 facilitates communications between the RFID element 108 of the patient tracking system 300, the RFID reader 415 of the medical document container 405, computing device 500A, and computing device 500B operated by a health care provider 540. The network 530 may be any wired or wireless local area network (LAN) and/or wide area network (WAN), such as an intranet, an extranet, or the Internet. In various embodiments, the network 530 uses standard communication technologies and/or protocols. Examples of technologies used by the network 530 include Ethernet, 802.11, 3G, 4G, 802.16, or any other suitable communication technology. The network 530 may use wireless, wired, or a combination of wireless and wired communication technologies. Examples of protocols used by the network 530 include transmission control protocol/Internet protocol (TCP/IP), hypertext transport protocol (HTTP), simple mail transfer protocol (SMTP), file transfer protocol (TCP), or any other suitable communication protocol.

Figure 5B:
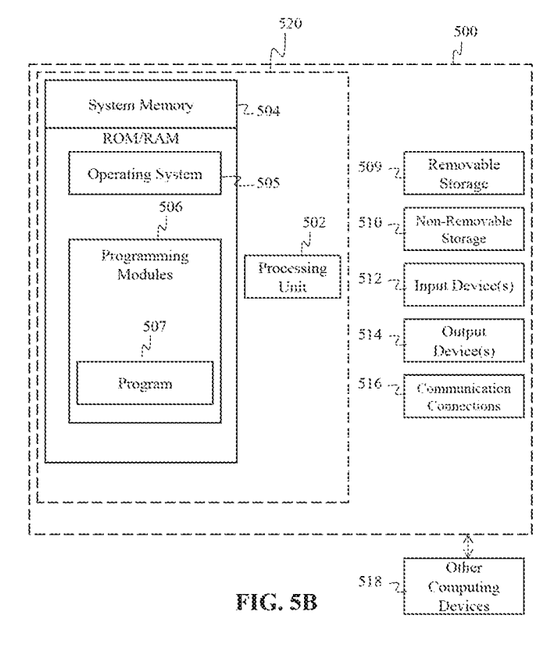
FIG. 5B is a block diagram of a system including an example computing device and other computing devices, in accordance with an embodiment.

FIG. 5B is a block diagram of an example computing device 500 (e.g., either computing device 500A or computing device 500B). Consistent with the embodiments described herein, the aforementioned actions performed by system or components thereof and may be implemented in a computing device. Any suitable combination of hardware, software, or firmware may be used to implement the computing device 500. The aforementioned system, device, and processors are examples and other systems, devices, and processors may comprise the aforementioned computing device.

With reference to FIG. 5B, a system consistent with an embodiment of the invention may include a plurality of computing devices, such as computing device 500. In a basic configuration, computing device 500 may include at least one processing unit 502 and a system memory 504. Depending on the configuration and type of computing device, system memory 504 may comprise, but is not limited to, volatile (e.g. random access memory (RAM)), non-volatile (e.g. read-only memory (ROM)), flash memory, or any combination or memory. System memory 504 may include operating system 505, one or more programming modules 506 (such as program module 507). Operating system 505, for example, may be suitable for controlling computing device operation. In one embodiment, programming modules 506 may include, for example, a program module 507. Furthermore, embodiments of the invention may be practiced in conjunction with a graphics library, other operating systems, or any other application program and is not limited to any particular application or system. This basic configuration is illustrated in FIG. 5B by those components within a dashed line 520.

Computing device 500 may have additional features or functionality. For example, computing device 500 may also include additional data storage devices (removable and/or non-removable) such as, for example, magnetic disks, optical disks, or tape. Such additional storage is illustrated in FIG. 5B by a removable storage 509 and a non-removable storage 510. Computer storage media may include volatile and nonvolatile, removable and non-removable media implemented in any method or technology for storage of information, such as computer readable instructions, data structures, program modules, or other data. System memory 504, removable storage 509, and non-removable storage 510 are all computer storage media examples (i.e. memory storage). Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512 such as a keyboard, a mouse, a pen, a sound input device, a camera, a touch input device, etc. Output device(s) 514 such as a display, speakers, a printer, etc. may also be included. The aforementioned devices are only examples, and other devices may be added or substituted.

Computing device 500 may also contain a communication connection 516 that may allow device 500 to communicate with other computing devices 518, such as over a network in a distributed computing environment, for example, an intranet or the Internet. Communication connection 516 is one example of communication media. Communication media may typically be embodied by computer readable instructions, data structures, program modules, or other data in a modulated data signal, such as a carrier wave or other transport mechanism, and includes any information delivery media.

As stated above, a number of program modules and data files may be stored in system memory 504, including operating system 505. While executing on processing unit 502, programming modules 506 may perform processes including performing sound processing functions such as signal processing, digital processing, etc. Computing device 500 may also include a graphics processing unit 503, which supplements the processing capabilities of processor 502 and which may execute programming modules 506, including all or a portion of those processes identified or alluded to above. The aforementioned processes are examples, and processing units 502 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, thumb drives, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A shield for reducing signal interference originating from a human individual, the shield configured to couple with a tracker device worn by a patient, the shield comprising:
   a base comprising a first side, second side, and a RFID element;
   an adhesive element coupled to the first side of the base, the adhesive element comprising an adhesive surface;
   a first non-conductive element; and
   a second non-conductive element, wherein the second non-conductive element is coupled to the second side of the base, and the first non-conductive element is coupled to the second non-conductive element.

2. The shield of claim 1, wherein a density of the first non-conductive element is less than a density of the second non-conductive element.

3. The shield of claim 2, wherein the first non-conductive element possesses a density between 3 kg/m$^3$ and 50 kg/m$^3$.

4. The shield of claim 2, wherein the second non-conductive element possesses a density between 50 kg/m$^3$ and 250 kg/m$^3$.

5. The shield of claim 1, wherein a thickness of the first non-conductive element is greater than a thickness of the second non-conductive element.

6. The shield of claim 1, wherein each of the first non-conductive element and second non-conductive element comprises an ethylene vinyl acetate material.

7. The shield of claim 1, wherein the base comprises a polypropylene material with a density between 500 and 1500 kg/m$^3$.

8. The shield of claim 1, wherein the adhesive element, the base, the first non-conductive element, and the second non-conductive element form sequential layers of the shield.

9. The shield of claim 1, wherein the RFID element comprises a passive RFID tag.

10. The shield of claim 9, wherein the RFID element is configured to receive an ultra-high frequency RF signal and transmit a signal comprising a location of the RFID element in response to receiving the ultra-high frequency RF signal.

11. A patient tracking system comprising:
   a tracker device comprising:
      an inner surface; and
      an outer surface comprising patient information; and
   a shield coupled to the tracker device, the shield comprising:
      a base comprising a first side, second side, and a RFID transmitter;
      an adhesive element coupled to the first side of the base, the adhesive element comprising an adhesive surface that is coupled to the inner surface of the tracker device;
      a first non-conductive element; and
      a second non-conductive element, wherein the second non-conductive element is coupled to the second side of the base, and the first non-conductive element is coupled to the second non-conductive element.

12. The patient tracking system of claim 11, wherein the tracker device is configured to be worn by a patient.

13. The patient tracking system of claim 11, wherein the tracker device is medical equipment.

14. The patient tracking system of claim 11, wherein a density of the first non-conductive element is less than a density of the second non-conductive element.

15. The patient tracking system of claim 14, wherein the first non-conductive element possesses a density between 3 kg/m$^3$ and 50 kg/m$^3$.

16. The patient tracking system of claim 14, wherein the second non-conductive element possesses a density between 50 kg/m$^3$ and 250 kg/m$^3$.

17. The patient tracking system of claim 11, wherein each of the first non-conductive element and second non-conductive element comprises an ethylene vinyl acetate material.

18. The patient tracking system of claim 11, wherein a thickness of the first non-conductive element is greater than a thickness of the second non-conductive element.

19. The patient tracking system of claim 11, wherein the base comprises a polypropylene material with a density between 500 and 1500 kg/m$^3$.

20. The patient tracking system of claim 11, wherein the RFID transmitter comprises a passive RFID tag that is configured to receive an ultra-high frequency RF signal and transmit a signal comprising a location of the RFID transmitter in response to receiving the ultra-high frequency RF signal.

21. The patient tracking system of claim 11, wherein the tracker device is one of a wristband, necklace, headband, or article of clothing.

22. The patient tracking system of claim 11, wherein the adhesive element, the base, the first non-conductive element, and the second non-conductive element form sequential layers of the shield.

* * * * *